United States Patent

McAlpine et al.

[11] 4,282,211
[45] Aug. 4, 1981

[54] 1-EPI-2-DEOXYFORTIMICIN B AND DERIVATIVES

[75] Inventors: James B. McAlpine, Libertyville; Ronald E. Carney, Gurnee, both of Ill.

[73] Assignee: Abbott Laboratories, Chicago, Ill.

[21] Appl. No.: 79,146

[22] Filed: Sep. 26, 1979

[51] Int. Cl.³ .................. A61K 31/71; C07H 15/22
[52] U.S. Cl. ............................ 424/180; 536/17 R
[58] Field of Search ................ 536/17 R, 17 B; 424/180, 181

[56] References Cited

U.S. PATENT DOCUMENTS

| 4,169,198 | 9/1979 | Martin et al. | 536/17 R |
| 4,176,178 | 11/1979 | Martin et al. | 536/17 R |
| 4,192,867 | 3/1980 | Martin et al. | 536/17 B |

Primary Examiner—Johnnie R. Brown
Attorney, Agent, or Firm—Robert L. Niblack; Gildo E. Fato; Joyce R. Niblack

[57] ABSTRACT

1-Epi-2-deoxyfortimicin B and 4-N-derivatives thereof represented by the formula:

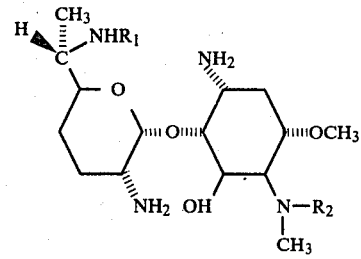

wherein: $R_1$ is hydrogen or loweralkyl and $R_2$ is selected from the group consisting of loweralkyl, aminoloweralkyl, diaminoloweralkyl, N-loweralkylaminoloweralkyl, N,N-diloweralkylaminoloweralkyl, hydroxyloweralkyl, N-loweralkylaminohydroxyloweralkyl, N,N-diloweralkylaminoloweralkyl, acyl, aminoacyl, diaminoacyl, hydroxyacyl, hydroxy-substituted aminoacyl hydroxy-substituted diaminoacyl, N-loweralkylaminoacyl, N,N-diloweralkylaminoacyl, hydroxy-substituted-N-loweralkylaminoacyl or hydroxysubstituted N,N-diloweralkylaminoacyl with the limitation that $R_2$ cannot be hydrogen glycyl, formylglycyl or hydantoyl, and the pharmaceutically acceptable salts thereof. The compounds are broad spectrum antibiotics.

14 Claims, No Drawings

1-EPI-2-DEOXYFORTIMICIN B AND DERIVATIVES

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide structures which are less toxic than the parent antibiotic. Further, in the same family series mentioned above, certain modifications alter the antibacterial spectrum advantageously either by increasing the intrinsic activity or increasing activity against resistant strains.

Further, historically, once an aminoglycoside antibiotic has been in clinical use for a period of time, resistant microorganisms develop. In many cases, the resistance is R-factor mediated and is attributed to the ability of the bacteria to enzymatically modify the amino or hydroxyl groups of the aminoglycoside antibiotics. Thus there is also a need for new entities which can be held in reserve to combat strains which have become resistant to treatment by the clinically used antibiotics.

The fortimicins are a relatively new class of aminoglycoside antibiotics. Fortimicin A is diclosed in U.S. Pat. No. 3,976,768 and fortimicin B in U.S. Pat. No. 3,931,400. Chemical modification of the parent fortimicins have been found to either increase the intrinsic activity of fortimicin A and B, reduce the toxicity or provide therapeutic agents which while having about the same activity, or perhaps somewhat weaker activity but nevertheless are useful as reserve antibiotics in the event resistant strains develop after a period of clinical use of one or more of the fortimicins. The 4-N-acyl derivatives of fortimicin B are disclosed in U.S. Pat. No. 4,091,032 as are the 4-N-alkylfortimicin B derivatives. The 3-O-demethylfortimicins A and B and fortimicin B derivatives are disclosed in U.S. Pat. No. 4,124,756. 2-Deoxyfortimicins A and B and 4-N-acyl and alkyl fortimicin B derivatives are disclosed in commonly assigned, U.S. Pat. Nos. 4,192,867 and 4,187,297 and the 1-epi-derivatives of fortimicins A and B and the 4-N-acyl and alkyl derivatives thereof are disclosed and claimed in commonly assigned, co-pending U.S. Patent application Ser. No. 025,221, filed Mar. 29, 1979. 1-Epi-2-deoxyfortimicin A has been produced by fermentation of a suitable Saccharopolyspora species, DT2813-021.

While a number of fortimicin derivatives have been made to date, and valuable therapeutic agents have been identified, the search continues for new fortimicin derivatives which either have a broader spectrum, less ototoxicity, exhibit oral activity, etc. as well as agents that can be held in reserve and used to treat infections caused by organisms which have become resistant to therapy with other fortimicins. The present invention provides one such class of fortimicins.

SUMMARY OF THE INVENTION

The present invention provides 1-epi-2-deoxyfortimicins which are useful as broad spectrum antibiotics in treating infections caused by susceptible strains of *Staphylococcus aureus, Enterobacter aerogenes, Escherichia coli, Klebsiella pneumoniae, Providencia stuartii, Pseudomonas aeruginosa, Salmonella typhimurium, Serratia marescens, Shigella sonnei, Proteus rettgeri, Proteus vulgaris* and *Proteus mirabilis*.

Intermediates useful in making the novel compounds as well as pharmaceuticals and methods are provided by the present invention.

DETAILED DESCRIPTION OF PREFERRED EMBODIMENTS

The fortimicin derivatives of this invention, 1-epi-2-deoxyfortimicin B and derivatives are represented by the Formula I:

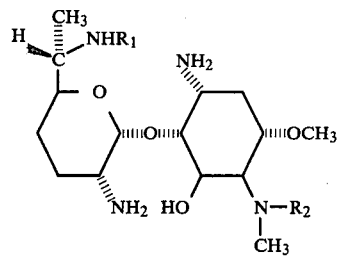

wherein $R_1$ is hydrogen or loweralkyl and $R_2$ is selected from the group consisting of loweralkyl, aminoloweralkyl, diaminoloweralkyl,N-loweralkylaminoloweralkyl,N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl, aminoacyl, diaminoacyl, hydroxyacyl, hydroxy-substituted amino acyl, hydroxy-substituted diaminoacyl, N-loweralkylaminoacyl, N,N-diloweralkylaminoacyl, hydroxy-substituted N-loweralkylaminoacyl or hydroxysubstituted N,N-diloweralkylaminoacyl with the limitation the $R_2$ cannot be hydrogen, glycyl, formylglycyl or hydantoyl, and the pharmaceutically acceptable salts thereof.

The term "loweralkyl", as used herein, refers to straight or branched chaim alkyl radicals having from 1 to 7 carbon atoms, including, but not limited to methyl, ethyl, n-propyl, iso-propyl, n-butyl, sec-butyl, tert-butyl, n-pentyl, 2-methylbutyl, 2,2-dimethylpropyl, n-hexyl, 2,2-dimethylbutyl, 1-methylpentyl, 2-methylpentyl, n-heptyl and the like.

The term "acyl" as used in the definition of $R_3$ in the specification and claims, refers to acyl groups represented by the formula

wherein $R_3$ is loweralkyl, i.e., acetyl, propionyl, butyryl, valeryl and the like.

The terms "aminoacyl" et seq. for $R_3$ include the naturally occurring amino acids such as glycyl, valyl, alanyl, sarcosyl, leucyl, isoleucyl, prolyl, seryl, and the like as well as groups such as 2-hydroxy-4-aminobutyryl. The amino acids residues included in the above terms can be in the L- or D- configurations or a mixture thereof, with the exception of course of glycyl.

The term "pharmaceutically acceptable salts", as used herein, refers to the non-toxic acid addition salts of the compounds of this invention which can be prepared in situ during the final isolation and purification or by separately reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salts of this invention can be per-N-salts.

The Compounds of Formula I, are useful as broad spectrum antibiotics when administered parenterally to a patient suffering from an infection caused by a susceptible strain of bacilli in dosages of from 10 to 100 mg/kg of body weight daily, based on lean body weight as is good medical practice with the aminoglycoside antibiotics, and preferably from about 15 to about 30 mg/kg of body weight daily. The compounds are preferably administered in divided doses, i.e. three to four times daily and can be administered by intravenous, intramuscular, intraperitoneal, or subcutaneous routes of administration for systemic activity and orally to sterilize the intestinal tract. The anitibiotics of this invention can also be administered in suppository form.

The antibiotics of Formula I can be used as described above in the treatment of infections caused by susceptible strains of organisms such as *Staphylococcus aureus, Enterobacter aerogenes, Escherichia coli, Klebsiella pneumoniae, Providencia stuartii, Pseudomonas aeruginosa, Salmonella typhimurium, Shigella sonnei, Proteus rettgeri Proteus vulgaris* and *Proteus mirabilis.*

The term "susceptible strains" refers to strains of bacilli which have been demonstrated to be sensitive to a particular antibiotic in a standard in vitro sensitivity test and thus in vitro activity has been established for a particular antibiotic against a specific strain of a specific organism.

The compounds of Formula I can also be incorporated into scrub solutions for sterilizing surfaces such as laboratory benchtops, operating room surfaces and the like.

The compounds of Formula I are prepared from 1-epi-2-deoxy-2-oxo-4-N-substituted-tetra-N-benzyloxcarbonylfortimicin B derivatives according to the procedure described in commonly assigned, co-pending United States Patent application Ser No. 025,211, filed Mar. 29, 1979.

Generally speaking, 1-epi-2-deoxy-2-oxo-tetra-N-benzyloxcarbonylfortimicin A is reduced with sodium borohydride to obtain 1-epi-tetra-N-benzloxycarbonylfortimicin A as the major product and 1,2-di-epi-tetra-N-fortimicin A as the minor product. The latter is 2-deoxygenated by treatment with thiocarbonyldiimidazole to obtain 2-thiocarbonylimidazolide of 1,2-di-epi-tetra-N-benzyloxycarbonylfortimicin A. Treatment of the latter with n-tributylstannane results in 1-epi-2-deoxy-tetra-N-benzyloxycarbonylfortimicin A. Deprotection results in 1-epi-2-deoxyfortimicin A which has heretofore been unobtainable by synthetic preparations.

By starting with the appropriate 4-N-derivative of 1-epi-2-deoxy-2-oxo-tetra-N-benzyloxcarbonylfortimicin B, the above procedure results in the desired 1-epi-2-deoxy-4-N-substituted fortimicin B derivative; i.e. 1-epi-2-deoxy-2-oxo-4-N-sarcosyl-tetra-N-benzyloxycarbonylfortimicin B, when subjected to the above procedure, results in 1-epi-2-deoxy-4-N-sarcosylfortimicin B. Likewise, 1-epi-2-deoxy-4-N-$\beta$-alanylfortimicin B, 1-epi-2-deoxy-4-N-$\beta$-aminoethylfortimicin B, 1-epi-2-deoxy-4-N-(2-hydroxy-4-aminobutyl)fortimicin B, 1-epi-2-deoxy-4-N-(2-hydroxy-4-aminobutyryl)fortimicin B, etc., can be prepared.

EXAMPLE 1

1-Epi-2-deoxy-2-oxo-tetra-N-benzyloxycarbonylfortimicin A

A solution of tetra-N-benzyloxycarbonylfortimicin A (5.0 g, 5.3 millimole) in acetone (100 ml) is treated at 4° C. with Jones Reagent (aqueous chromic acid in acetone, 4.0 ml). The mixture is maintained at 4° C. for 35 minutes and poured into water (7 volumes). The products are extracted with methylene chloride and the solution dried over magnesium sulfate. Solvent is removed and the residue is chromatographed over a column of silica gel to give 1-epi-2-deoxy-2-oxo-tetra-N-benzyloxycarbonylfortimicin A(1.81 g).

Analysis calcd. for $C_{49}H_{57}N_5O_{14}$: C,62.61; H,6.11; N,7.45. Found: C,62.74; H,6.03; N,7.43.

1,2-Di-epi-tetra-N-benzyloxycarbonylfortimicin A

1-Epi-2-deoxy-2-oxo-tetra-N-benzyloxycarbonylfortimicin A(25 g, 26.5 millinole) is dissolved in chloroform (400 ml) and treated with sodium borohydride(400 mg) at room temperature. The mixture is stirred for 72 hours. The excess borohydride is consumed by the addition of acetone and the mixture is evaporated to dryness under reduced pressure.

The residue is dissolved in a minimum volume of dichloroethane-ethanol(24:1,v/v) and chromatographed over a column of silica gel(7 cm×70 cm) packed in the same solvent system to afford 1.8 g of the desired product.

EXAMPLE 3

1-Epi-tetra-N-benzyloxycarbonylfortimicin A-2-epi-thiocarbonylimidazolide 1,2-Epi-tetra-N-benzyloxycarbonylfortimicin A(300 mg, 0.318 millimole) is dissolved in ethyl acetate(15 ml) and treated with N,N'-thiocarbonyldiimidazole(200 mg) under reflux for 6½ hours. Solvent is removed under reduced pressure. The residue is dissolved in a minimum volume of dichloroethane-ethanol[24:1(v/v)] and chromatographed over a column of silica gel(1.8 cm×50 cm) to yield 70 mg of the desired product.

EXAMPLE 4

1-Epi-2-deoxy-tetra-N-benzyloxycarbonylfortimicin A

1-Epi-tetra-N-benzyloxycarbonylfortimicin A-2-epi-thiocarbonylimidazolide(70 mg) is dissoved in dioxane(15 ml) and the solution is added dropwise to a solution of tri-n-butylstannane(0.15 ml) in dioxane(12 ml) and heated under reflux in an atmosphere of nitrogen for 2 hours. The reaction mixture is evaporated to dryness under reduced pressure. The residue is dissolved in a minimum volume of ethyl acetate and chromatographed over a column of silica gel(1.8 cm×65 cm) to afford 40 mg of product.

EXAMPLE 5

1-Epi-2-deoxyfortimicin A tetrahydrochloride

1-Epi-2-deoxy-tetra-N-benzyloxycarbonylfortimicin A (40 mg) is dissolved in 0.2 M methanolic hydrogen chloride and hydrogenolyzed over 5% palladium on carbon(40 mg) at 3 atmospheres of pressure for 4 hours. The catalyst is removed by filtration and the filtrate evaporated to dryness under reduced pressure to give 28 mg of product.

EXAMPLE 6

1-Epi-2-deoxy-2-oxo-4-N-sarcosyl-tetra-N-benzyloxycarbonylfortimicin B

By substituting 4-N-sarconsyl-tetra-N-benzyloxycarbonylfortimicin B for the starting intermediate of Example 1, 1-epi-2-deoxy-2-oxo-4-N-sarcosyl-tetra-N-benzyloxycarbonylfortimicin B is obtained.

EXAMPLE 7

1,2-Di-epi-4-N-sarcosyl-tetra-N-benzyloxycarbonylfortimicin B 1,2-Di-epi-4-N-sarcosyl-tetra-N-benzyloxycarbonylfortimicin B is obtained according to the method of Example 2 by treating the compound of Example 6 with sodium borohydride.

EXAMPLE 8

1-Epi-4-N-sarcosyl-tetra-N-benzyloxycarbonylfortimicin B-2-epi-thiocarbonylimidazole Treatment of the compound of Example 7 with N,N-thiocarbonyldiimidazole according to the method of Example 3 results in 1-epi-4-N-sarcosyl-tetra-N-benzyloxycarbonylfortimicin B-2-epi-thiocarbonylimidazole.

EXAMPLE 9

1-Epi-2-deoxy-4-N-sarcosyl-tetra-N-benzyloxycarbonylfortimicin B

Treatment of the compound of Example 8 with tri-n-butylstannane according to the method of Example 4 results in 1-epi-2-deoxy-4-N-sarcosylfortimicin B.

EXAMPLE 10

1-Epi-2-deoxy-4-N-sarcosylfortimicin B tetrahydrochloride

Deprotection of the compound of Example 9 according to the method of Example 5 yields 1-epi-2-deoxy-4-N-sarcosylfortimicin B tetrahydrochloride.

EXAMPLE 11

1-Epi-2-deoxy-2-oxo-4-N-$\beta$-alanyl-tetra-N-benzyloxycarbonylfortimicin B

By substituting 4-N-$\beta$-alanyl-tetra-N-benzyloxycarbonylfortimicin B for the intermediate of Example 1, 1-epi-2-deoxy-2-oxo-4-N-$\beta$-alanyl-tetra-N-benzyloxycarbonylfortimicin B is obtained.

EXAMPLE 12

1,2-Di-epi-4-N-$\beta$-alanyl-tetra-N-benzyloxycarbonylfortimicin B

Treatment of the compound of Example 11 with sodium borohydride according to the method of Example 2 results in 1,2-di-epi-4-N-$\beta$-alanyl-tetra-N-benzyloxycarbonylfortimicin B.

EXAMPLE 13

1-Epi-4-N-$\beta$-alanyl-tetra-N-benzyloxycarbonylfortimicin B-2-epi-thiocarbonylimidazole Treatment of the compound of Example 12 with N,N-thiocarbonylimidazole according to the method of Example 3 results in the title compound.

EXAMPLE 14

1-Epi-2-dexoy-4-N-$\beta$-alanyl-tetra-N-benzyloxycarbonylfortimicin B

Treatment of the compound of Example 13 with n-tributylstannane according to the method of Example 4 results in the title compound.

EXAMPLE 15

1-Epi-2-deoxy-4-N-$\beta$-alanylfortimicin B tetrahydrochloride

Deprotection of the compound of Example 14 according to the method of Example 5 results in 1-epi-2-deoxy-4-N-$\beta$-alanylfortimicin B tetrahydrochloride.

It will be apparent to those skilled in the art that by starting with the appropriate 4-N-tetra-N-protected derivative of fortimicin B, the desired 1-epi-2-deoxy-4-N-substituted fortimicin B derivative can be obtained following the procedures set forth in Examples 1–15 herein.

For example, by substituting 4-$\beta$-aminoethyl-tetra-N-benzyloxycarbonylfortimicin B for the starting material of Example 1,1-epi-2-deoxy-4-$\beta$-aminoethylfortimicin B tetrahydrochloride is obtained. Similarly, 1-epi-2-deoxy-4-N-(2-hydroxy-4-aminobutyl)fortimicin B tetrahydrochloride, 1-epi-2-deoxy-4-N-(2-hydroxy-4-aminobutyryl)fortimicin B tetrahydrochloride, etc. can be obtained.

1-Epi-fortimicin B derivatives can be prepared by removing the C$_4$N-glycyl moiety from 1-epi-fortimicin A by basic or acidic hydrolysis, using, for example, 0.2 N methanolic sodium hydroxide to obtain 1-epi-fortimicin B. 1-Epi-fortimicin B can then be selectively protected at the three primary amino groups by treatment with, for example, the N-hydroxysuccinimide ester of benzyloxycarbonate or a similar active ester such as those described in U.S. Pat. No. 4,091,032 which discloses the 4-N-acyl derivatives of fortimicin B and their method of preparation which is generally followed in the preparation of the corresponding 1-epi-derivatives of this invention.

The per-N-protected intermediate can then be reacted with a carboxylic acid derivative such as a carboxylic acid ester or a carboxylic acid azide, following the methodology set forth in U.S. Pat. No. 4,091,032 and that commonly used in peptide synthesis to obtain the desired 4-N-acyl(using the term broadly to include aminoacyl, hydroxyacyl, etc.) intermediates. The above-referred to active carboxylic acid esters can be prepared by reacting the approrpirate carboxylic acid, R$_3$COOH with, for example 1-hydroxybenzotriazole-N-hydroxysuccinimide, N-hydroxy-5-norbornene-2,3-dicarboximide, etc. according to the method of Fugino et al. *Chem Phar. Bull.* Japan 22, 1857 (1974).

The 4-N-alkyl derivatives of this invention are obtained by reduction of the C$_4$-amides to the corresponding C$_4$-alkyl derivatives by treatment with diborane.

6'-N-methylation can be conveniently effected by subjecting the 1-epi-fortimicin to be 6'-N-methylated to selective N-carbobenzyloxylation with one mole of an active ester of benzylcarbonate, and reducing the 6'-N-carbobenzoxy derivative with a suitable metal hydride such as lithium aluminum hydride as taught by Umezawa et al. U.S. Pat. No. 3,925,353 and in commonly assigned co-pending U.S. Pat. application Ser. No. 863,108 which discloses the 6'-N-alkyl derivatives of fortimicin A and B and the 4-N-acyl and alkyl fortimicin B derivatives.

Other alkyl groups can be attached at the 6'-N-position by treating the 1-epi-fortimicin to be 6'-N-alkylated with one mole of the appropriate aldehyde and reducing the resulting Schiff base with hydrogen in the presence of a precious metal catalyst such as platinum oxide or with a suitable metal hydride such as sodium cyanoborohydride.

We claim:

1. A 1-epi-fortimicin represented by the formula

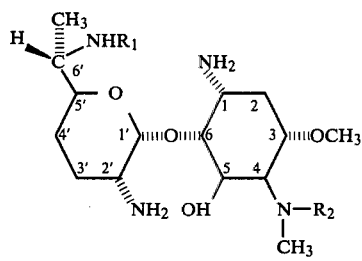

wherein: $R_1$ is hydrogen or loweralkyl; and $R_2$ is selected from the group consisting of loweralkyl, aminoloweralkyl, diaminoloweralkyl, N-loweralkylaminoloweralkyl, N,N-diloweralkylaminoloweralkyl, hydroxyloweralkyl, N-loweralkylaminohydroxyloweralkyl, N,N-diloweralkylaminohydroxyloweralkyl, acyl, aminoacyl, diaminoacyl, hydroxyacyl, hydroxy-substituted aminoacyl, N-loweralkylaminoacyl, N,N-diloweralkylaminoacyl, hydroxy-substituted-N-loweralkylaminoacyl and hydroxy-substituted N,N-diloweralkylaminoacyl; with the limitation that $R_2$ cannot be glycyl, formylglycyl or hydantoyl; and the pharmaceutically acceptable salts thereof.

2. A compound of claim 1 wherein $R_1$ is hydrogen.
3. A compound of claim 2 wherein $R_1$ is methyl.
4. A compound of claim 1: 1-epi-2-deoxy-4-N-$\beta$-alanylfortimicin B or a pharmaceutically acceptable salts thereof.
5. A compound of claim 1: 1-epi-2-deoxy-4-N-sarcosylfortimicin B or a pharmaceutically acceptable salt thereof.
6. A compound of claim 1: 1-epi-2-deoxy-4-N-(2-hydroxy-4-aminobutyl)fortimicin B or a pharmaceutically acceptable salt thereof.
7. A compound of claim 1: 1-epi-2-deoxy-4-N-(2-hydroxy-4-aminobutyryl)fortimicin B or a pharmaceutically acceptable salt thereof.
8. A compound of claim 4: 1-epi-2-deoxy-4-N-$\beta$-alanylfortimicin B tetrahydrochloride.
9. A compound of claim 5: 1-epi-2-deoxy-4-N-sarcosylfortimicin B tetrahydrochloride.
10. A compound of claim 6: 1-epi-2-deoxy-4-N-(2-hydroxy-4-aminobutyl)fortimicin B tetrahydrochloride.
11. A compound of claim 7: 1-epi-2-deoxy-4-N-(2-hydroxy-4-aminobutyryl)fortimicin B tetrahydrochloride.
12. A pharmaceutical composition comprising an anti-bacterially effective amount of a compound of claim 1 and a pharmaceutically acceptable carrier or diluent.
13. A composition of claim 12 wherein said compound of claim 1 is 1-epi-2-deoxy-4-N-$\beta$-alanylfortimicin B or a pharmaceutically acceptable salt thereof.
14. A composition of claim 12 wherein said compound of claim 1 is 1-epi-2-deoxy-4-N-sarcosylfortimicin B or a pharmaceutically acceptable salt thereof.

* * * * *